United States Patent [19]

Deana et al.

[11] Patent Number: 5,504,115
[45] Date of Patent: Apr. 2, 1996

[54] INHIBITORS OF FARNESYL PROTEIN TRANSFERASE

[75] Inventors: Albert A. Deana, deceased, late of Lansdale, by Ermelinda S. Deana, legal representative; S. Jane deSolms, Norristown; Samuel L. Graham, Schwenksville; Robert L. Smith, Lansdale, all of Pa.

[73] Assignee: Merck & Co., Inc., Rahway, N.J.

[21] Appl. No.: 267,088

[22] Filed: Jun. 28, 1994

Related U.S. Application Data

[62] Division of Ser. No. 905,927, Jun. 26, 1992, Pat. No. 5,352,705.

[51] Int. Cl.$^6$ .......................... A61K 31/16; C07C 237/06
[52] U.S. Cl. .......................... 514/616; 514/399; 514/602; 514/605; 514/630; 514/617; 514/618; 514/620; 514/649; 530/323; 548/309.7; 564/84; 564/92; 564/152; 564/154; 564/197; 564/155; 564/162; 564/164; 564/196
[58] Field of Search .......................... 564/154; 514/618, 514/616, 617, 595, 596, 626, 617, 620, 630, 605; 435/15; 530/323

[56] References Cited

U.S. PATENT DOCUMENTS

| | | | |
|---|---|---|---|
| 5,043,268 | 8/1991 | Stock | 435/15 |
| 5,124,322 | 6/1992 | Hughes | 564/154 |
| 5,331,099 | 7/1994 | Stern et al. | 564/154 |
| 5,352,705 | 10/1994 | Deana et al. | 514/630 |
| 4,929,6741 | 5/1990 | Haslanger et al. | 564/154 |

FOREIGN PATENT DOCUMENTS

| | | | |
|---|---|---|---|
| 0322184 | 6/1989 | European Pat. Off. | 564/154 |
| 0456180A1 | 11/1991 | European Pat. Off. | C12N 9/10 |
| WO91/16340 | 10/1991 | WIPO | C07K 7/06 |

OTHER PUBLICATIONS

Goldstein, J. L., et al., "Nonfarnsylated Tetrapeptide Inhibitors of Protein Farnesyltransferase", The Journal of Biological Chemistry, vol. 266, No. 24, pp. 15575–15578 (1991).

Kohl, N. E. et al., "Protein farnesyltransferase inhibitors block the growth of ras-dependent tumors in nude mice", Proc. Natl. Acad. Sci. USA, vol. 91, pp. 9141–9145 (1994).

Primary Examiner—Shailendra Kumar
Attorney, Agent, or Firm—David A. Muthard; Mark R. Daniel

[57] ABSTRACT

The present invention is directed to compounds which inhibit farnesyl-protein transferase (FTase) and the farnesylation of the oncogene protein Ras. The invention is further directed to chemotherapeutic compositions containing the compounds of this invention and methods for inhibiting farnesyl-protein transferase and the farnesylation of the oncogene protein Ras.

4 Claims, No Drawings

INHIBITORS OF FARNESYL PROTEIN TRANSFERASE

This is a division of application Ser. No. 07/905,927 filed Jun. 26, 1992, now U.S. Pat. No. 5,352,705.

BACKGROUND OF THE INVENTION

The Ras gene is found activated in many human cancers, including colorectal carcinoma, exocrine pancreatic carcinoma, and myeloid leukemias. Biological and biochemical studies of Ras action indicate that Ras functions like a G-regulatory protein, since Ras must be localized in the plasma membrane and must bind with GTP in order to transform cells (Gibbs, J. et al., *Microbiol. Rev.* 53:171–286 (1989). Forms of Ras in cancer cells have mutations that distinguish the protein from Ras in normal cells.

At least 3 post-translational modifications are involved with Ras membrane localization, and all 3 modifications occur at the C-terminus of Ras. The Ras C-terminus contains a sequence motif termed a "CAAX" or "Cys-Aaa$^1$-Aaa$^2$-Xaa" box (Aaa is an aliphatic amino acid, the Xaa is any amino acid) (Willumsen et al., *"Nature"* 310:583–586 (1984)). Other proteins having this motif include the Ras-related GTP-binding proteins such as Rho, fungal mating factors, the nuclear lamins, and the gamma subunit of transducin.

Farnesylation of Ras by the isoprenoid farnesyl pyrophosphate (FPP) occurs in vivo on Cys to form a thioether linkage (Hancock et al., *Cell* 57:1167 (1989); Casey et al., *Proc. Natl. Acad. Sci. USA* 86:8323 (1989)). In addition, Ha-Ras and N-Ras are palmitoylated via formation of a thioester on a Cys residue near a C-terminal Cys farnesyl acceptor (Gutierrez et al., *EMBO J.* 8:1093–1098 (1989); Hancock et al., *Cell* 57:1167–1177 (1989)). Ki-Ras lacks the palmitate acceptor Cys. The last 3 amino acids at the Ras C-terminal end are removed proteolytically, and methyl esterification occurs at the new C-terminus (Hancock et al., ibid). Fungal mating factor and mammalian nuclear lamins undergo identical modification steps (Anderegg et al., *J. Biol. Chem.* 263:18236 (1988); Farnsworth et al., *J. Biol. Chem.* 264:20422 (1989)).

Inhibition of Ras farnesylation in vivo has been demonstrated with lovastatin (Merck & Co., Rahway, N.J.) and compactin (Hancock et al., ibid; Casey et al., ibid; Schafer et al., *Science* 245:379 (1989)). These drugs inhibit HMG-CoA reductase, the rate limiting enzyme for the production of polyisoprenoids and the farnesyl pyrophosphate precursor. It has been shown that a farnesyl-protein transferase using farnesyl pyrophosphate as a precursor is responsible for Ras farnesylation. (Reiss et al., *Cell*, 62:81–88 (1990); Schaber et al., *J. Biol. Chem.*, 265:14701–14704 (1990); Schafer et al., *Science*, 249:1133–1139 (1990); Manne et al., *Proc. Natl. Acad. Sci USA*, 87:7541–7545 (1990)).

Inhibition of farnesyl-protein transferase and, thereby, of farnesylation of the Ras protein, blocks the ability of Ras to transform normal cells to cancer cells. The compounds of the invention inhibit Ras farnesylation and, thereby, generate soluble Ras which, as indicated infra, can act as a dominant negative inhibitor of Ras function. While soluble Ras in cancer cells can become a dominant negative inhibitor, soluble Ras in normal cells would not be an inhibitor.

A cytosol-localized (no Cys-Aaa$^1$-Aaa$^2$-Xaa box membrane domain present) and activated (impaired GTPase activity, staying bound to GTP) form of Ras acts as a dominant negative Ras inhibitor of membrane-bound Ras function (Gibbs et al., *Proc. Natl. Acad. Sci. USA* 86:6630–6634 (1989)). Cytosollocalized forms of Ras with normal GTPase activity do not act as inhibitors. Gibbs et al., ibid, showed this effect in *Xenopus oocytes* and in mammalian cells.

Administration of compounds of the invention to block Ras farnesylation not only decreases the amount of Ras in the membrane but also generates a cytosolic pool of Ras. In tumor cells having activated Ras, the cytosolic pool acts as another antagonist of membrane-bound Ras function. In normal cells having normal Ras, the cytosolic pool of Ras does not act as an antagonist. In the absence of complete inhibition of farnesylation, other farnesylated proteins are able to continue with their functions.

Farnesyl-protein transferase activity may be reduced or completely inhibited by adjusting the compound dose. Reduction of farnesyl-protein transferase enzyme activity by adjusting the compound dose would be useful for avoiding possible undesirable side effects resulting from interference with other metabolic processes which utilize the enzyme.

These compounds and their analogs are inhibitors of farnesyl-protein transferase. Farnesyl-protein transferase utilizes farnesyl pyrophosphate to covalently modify the Cys thiol group of the Ras CAAX box with a farnesyl group. Inhibition of farnesyl pyrophosphate biosynthesis by inhibiting HMG-CoA reductase blocks Ras membrane localization in vivo and inhibits Ras function. Inhibition of farnesyl-protein transferase is more specific and is attended by fewer side effects than is the case for a general inhibitor of isoprene biosynthesis.

Previously, it has been demonstrated that tetrapeptides containing cysteine as an amino terminal residue with the CAAX sequence inhibit Ras farnesylation (Schaber et al., ibid; Reiss et. al., ibid; Reiss et al., *PNAS*, 88:732–736 (1991)). Such inhibitors may inhibit while serving as alternate substrates for the Ras farnesyl-transferase enzyme, or may be purely competitive inhibitors. (International Patent Publication WO 91/16340, University of Texas).

The compounds of the present invention are dipeptide-based amides which are potent inhibitors of Ras farnesyl-transferase. It is, therefore, an object of this invention to develop dipeptide-based amide compounds which will inhibit farnesyl-protein transferase and the farnesylation of the oncogene protein Ras. It is a further object of this invention to develop chemotherapeutic compositions containing the compounds of this invention, and methods for producing the compounds of this invention.

SUMMARY OF THE INVENTION

The present invention includes dipeptide-based amide compounds which inhibit farnesyl-protein transferase and the farnesylation of the oncogene protein Ras, chemotherapeutic compositions containing the compounds of this invention, and methods for producing the compounds of this invention.

The compounds of this invention are illustrated by the formula:

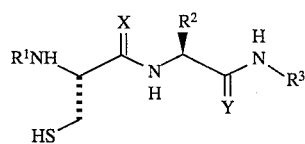

DETAILED DESCRIPTION OF THE INVENTION

The dipeptide-based amide compounds of this invention are useful in the inhibition of farnesyl-protein transferase and the farnesylation of the oncogene protein Ras. The compounds of this invention are illustrated by the formula:

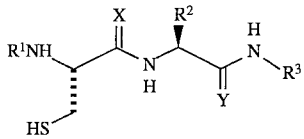

wherein:

X and Y are independently $H_2$ or O;

$R^1$ is an alkyl group, hydrogen, an acyl group, an alkylsulfonyl group or arylsulfonyl group, wherein alkyl and acyl groups comprise straight chain or branched chain hydrocarbons of 1 to 6 carbons atoms, which alternatively may be substituted with an aryl group;

$R^2$ is the side chains of naturally occurring amino acids, or in the alternative may be substituted or unsubstituted aliphatic, aromatic or heterocyclic groups, such as allyl, cyclohexyl, phenyl, pyridyl, imidazolyl or saturated chains of 2 to 8 carbon atoms which may be branched or unbranched, wherein the aliphatic substituents may be substituted with an aromatic or heteroaromatic ring;

$R^3$ is an aromatic or heteroaromatic ring or in the alternative an alkyl group or an aryl or heteroaryl substituted alkane, wherein the aromatic ring is unsubstituted or in the alternative, substituted with one or more groups which may be alkyl, halo, alkoxy, trifluoromethyl, or sulfamoyl groups, and which may be polycyclic.

or the pharmaceutically acceptable salts thereof.

The preferred compounds of this invention are as follows:

N-[2(R)-Amino-3-mercaptopropyl]-L-isoleucine-phenethylamide,

N-[2(R)-Amino-3-mercaptopropyl]-L-isoleucine-benzylamide,

N-[2(R)-Amino-3-mercaptopropyl]-L-isoleucine-3-methylbutylamide,

N-[2(R)-Amino-3-mercaptopropyl]-L-isoleucine- 3-phenylpropylamide,

N-[2(R)-Amino-3-mercaptopropyl]-L-isoleucyl-L-phenylalaninol,

N-[2(R)-Amino-3-mercaptopropyl]-L-isoleucine-N' -methylbenzylamide,

N-[2(R)-Amino-3-mercaptopropyl]-L-isoleucine-( 4-methoxybenzyl)amide,

N-[2(R)-Amino-3-mercaptopropyl]-L-isoleucine-( 2,4-dichlorobenzyl)amide,

N-[2(R)-Amino-3-mercaptopropyl]-L-isoleucine-( 4-trifluoromethylbenzyl)amide,

N-[2(R)-Amino-3-mercaptopropyl]-L-isoleucine-( 2,4-dichlorophenethyl)amide,

N-[2(R)-Amino-3-mercaptopropyl]-L-isoleucine-( 2-benzimidazolylmethyl)amide,

N-[2(R)-Amino-3-mercaptopropyl]-L-isoleucine-( 1-indanyl)amide,

N-[2(R)-Amino-3-mercaptopropyl]-L-isoleucine-( 2,4-dimethylbenzyl)amide,

N-[2(R)-Amino-3-mercaptopropyl]-L-isoleucine-( 2,3-dichlorobenzyl)amide,

N-[2(R)-Amino-3-mercaptopropyl]-L-isoleucine-( 4-sulfamoylbenzyl)amide,

N-[2(R)-Amino-3-mercaptopropyl]-L-isoleucine-anilide,

N-[2(R)-Amino-3-mercaptopropyl]-L-isoleucine-( 2,4-dimethylphenyl)amide,

N-[2(R)-Amino-3-mercaptopropyl]-L-isoleucine-( 2,3-dimethylphenyl)amide,

L-Cysteinyl-L-isoleucine-phenethylamide,

N-[2(S)-[2(R)-Amino-3-mercaptopropylamino]-3-methylpentyl] phenethylamine,

N-(2(R)-Amino-3-mercaptopropyl)-L-alanine-benzylamide,

N-Benzyl-[2(S)-(2(R)-Amino-3-mercaptopropyl)amino]-butyramide,

N-(2(R)-Amino-3-mercaptopropyl)-L-norleucine-benzylamide, or

N-(2(R)-Amino-3-mercaptopropyl)-L-norvaline-benzylamide.

The most preferred compounds of this invention are as follows:

N-[2(R)-Amino-3-mercaptopropyl]-L-isoleucine-3-chlorophenethylamide

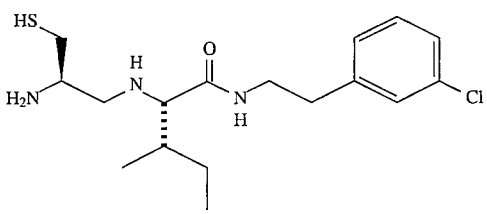

N-[2(R)-Amino-3-mercaptopropyl]-L-isoleucine-2,3-dichlorobenzylamide

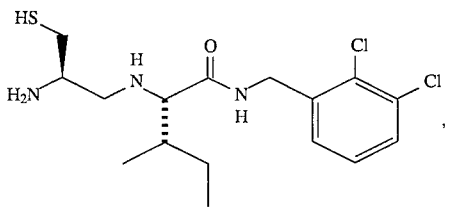

N-[2(R)-amino-3-mercaptopropyl]-L-isoleucine-anilide

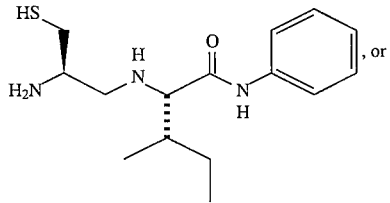

, or

N-[2(R)-amino-3-mercaptopropyl]-L-isoleucine-2,3-dimethylphenylamide

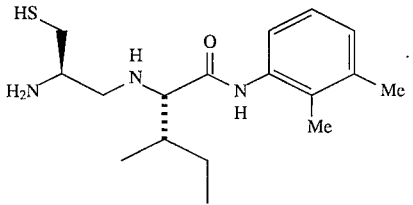

In the present invention, the amino acids which are disclosed are identified both by conventional 3 letter and single letter abbreviations as indicated below:

| Alanine | Ala | A |
| --- | --- | --- |
| Arginine | Arg | R |
| Asparagine | Asn | N |
| Aspartic acid | Asp | D |
| Asparagine or Aspartic acid | Asx | B |
| Cysteine | Cys | C |
| Glutamine | Gln | Q |
| Glutamic acid | Glu | E |
| Glutamine or Glutamic acid | Glx | Z |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

The pharmaceutically acceptable salts of the compounds of this invention include the conventional non-toxic salts of the compounds of this invention as formed, e.g., from non-toxic inorganic or organic acids. For example, such conventional non-toxic salts include those derived from inorganic acids such as hydrochloric, hydrobromic, sulfuric, sulfamic, phosphoric, nitric and the like: and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like.

The pharmaceutically acceptable salts of the compounds of this invention can be synthesized from the compounds of this invention which contain a basic moiety by conventional chemical methods. Generally, the salts are prepared by reacting the free base with stoichiometric amounts or with an excess of the desired salt-forming inorganic or organic acid in a suitable solvent or various combinations of solvents.

The compounds of the invention can be synthesized from their constituent amino acids by conventional peptide synthesis techniques, and the additional methods described below.

Standard methods of peptide synthesis are disclosed, for example, in the following works: Schroeder et al., "The Peptides", Vol. I, Academic Press 1965, or Bodanszky et al., "Peptide Synthesis", Interscience Publishers, 1966, or McOmie (ed.) "Protective Groups in Organic Chemistry", Plenum Press, 1973, or Barany et al., "The Peptides: Analysis, Synthesis, Biology" 2, Chapter 1, Academic Press, 1980, or Stewart et al., "Solid Phase Peptide Synthesis", Second Edition, Pierce Chemical Company, 1984. The teachings of these works are hereby incorporated by reference.

The compounds of this invention are prepared according to the reaction Scheme as set forth below:

REACTION SCHEME

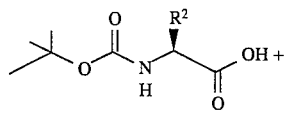

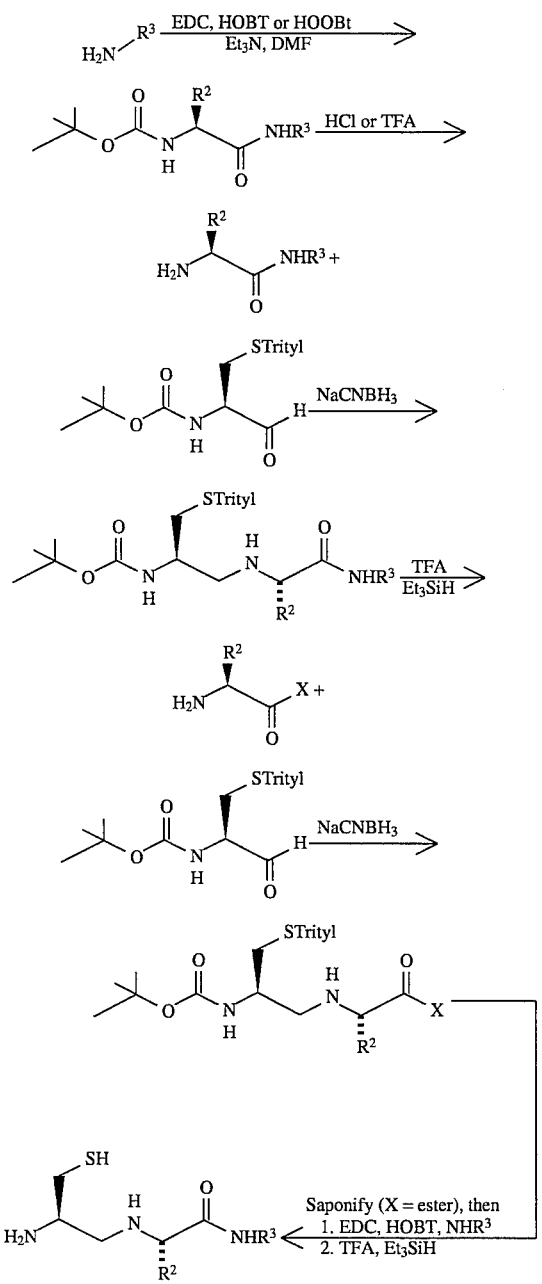

where X is OH or an ester.

In the first reaction scheme, coupling of a protected amino acid with the appropriate amine is accomplished using standard peptide coupling conditions. The resulting amino acid amide is deprotected and the primary amine is reductively alkylated with a protected cysteine-derived aldehyde using sodium cyanoborohydride or sodium triacetoxyborohydride. Finally, removal of the protecting groups provides the compounds of interest.

In the second scheme, a different strategy for synthesis is described. Reductive alkylation of an amino acid provides a protected dipeptide isostere. The same versatile intermediate can be obtained by reductive alkylation of an amino acid ester followed by saponification. This intermediate can be coupled with any of a number of amines using standard peptide coupling conditions. Deprotection provides the active farnesyl transferase inhibitors.

The choice of protecting groups shown in the scheme is not unique and the chemical reactions employed in these syntheses are compatible with other amine and sulfur protecting groups commonly used in peptide synthesis.

The compounds of this invention inhibit farnesyl-protein transferase and the farnesylation of the oncogene protein Ras. These compounds are useful as pharmaceutical agents for mammals, especially for humans. These compounds may be administered to patients for use in the treatment of cancer. Examples of the type of cancer which may be treated with the compounds of this invention include, but are not limited to, colorectal carcinoma, exocrine pancreatic carcinoma, and myeloid leukemias.

The compounds of this invention may be administered to mammals, preferably humans, either alone or, preferably, in combination with pharmaceutically acceptable carriers or diluents, optionally with known adjuvants, such as alum, in a pharmaceutical composition, according to standard pharmaceutical practice. The compounds can be administered orally or parenterally, including intravenous, intramuscular, intraperitoneal, subcutaneous, rectal and topical administration.

For oral use of a chemotherapeutic compound according to this invention, the selected compounds may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

The present invention also encompasses a pharmaceutical composition useful in the treatment of cancer, comprising the administration of a therapeutically effective amount of the compounds of this invention, with or without pharmaceutically acceptable carriers or diluents. Suitable compositions of this invention include aqueous solutions comprising compounds of this invention and pharmacologically acceptable carriers, e.g. saline, at a pH level, e.g.,7.4. The solutions may be introduced into a patient's intramuscular blood-stream by local bolus injection.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a human patient undergoing treatment for cancer. Administration occurs in an amount between about 0.1 mg/kg of body weight to about 20 mg/kg of body weight of a mammal per day, preferably of between 0.5 mg/kg of body weight to about 10 mg/kg of body weight of a mammal per day.

EXAMPLES

Examples provided are intended to assist in a further understanding of the invention. Particular materials employed, species and conditions are intended to be further illustrative of the invention and not limitative of the reasonable scope thereof.

Example 1

N-[2(R)-Amino-3-mercaptopropyl]-L-isoleucine-phenethylamide

Step A 2(R)-t-Butoxycarbonylamino-3-triphenyl-methylmercaptopropanal

The aldehyde was synthesized by the method described by Goel, et. al., [Organic Syntheses, 67, 69 (1988)] for the preparation of leucine aldehyde, with minor modification. These modifications were: substitution of isobutyl chloroformate for methyl chloroformate; and substitution of 10% citric acid for the dilute hydrochloric acid solutions used in the cited reference. The aldehyde is obtained as white foam.
$^1$H NMR (CDCl$_3$)δ 9.64 (S, 1H), 7.42 (m, 6H), 7.28 (m, 9H), 2.45 (m, 2H), 2.38 (m, 2H).

Step B N-[2(R)-(t-butoxycarbonyl)amino-3-triphenyl-methylmercaptopropyl]-L-isoleucine methyl ester L-Isoleucine methyl ester hydrochloride (1.82 g, 0.01 mol) and 2(R)-t-butoxycarbonylamino- 3-triphenyl-methylmercaptopropanal (4.48 g, 0.01 mol) were dissolved in EtOH (100 mL). 3 Å molecular sieves (6 g) and solid sodium cyanoborohydride (0.31 g, 0.005 mol) were added and the mixture was stirred at ambient temperature for 24 h. The reaction mixture was filtered, concentrated to dryness and chromatographed (SiO$_2$) with CHCl$_3$: MeOH, 99:1 to give 1.63 g of the title compound (28%).
$^1$H NMR (CDCl$_3$) δ 7.4–7.2 (m, 15H), 4.6–4.7 (m, 1H), 3.70 (s, 3H), 2.9–3.0 (m, 1H), 2.9–3.0 (m, 1H), 2.6–2.7 (m, 1H), 2.3–2.45 (m, 2H), 1.5–1.7 (m, 2H), 1.43 (s, 9H), 1.05–2.0 (m, 1H), 0.8–1.0 (m, 6H). Mass spectrum (FAB) 577 (M+1).

Step C N-[2(R)-(t-butoxycarbonyl)amino-3-triphenylmethylmercaptopropyl]-L-isoleucine N-[2(R)-(t-butoxycarbonyl)amino-3-triphenyl-methylmercaptopropyl] -L-isoleucine methyl ester (1.63 g, 0.0028 mol) was dissolved in MeOH (50 mL) and 1N NaOH solution (11.23 mL, 0.0112 mol) was added with stirring at ambient temperature. After 4 h, solid NaOH (2.0 g) was added and stirring was continued for 16 h. The reaction mixture was concentrated to remove MeOH and extracted with EtOAc (2×100 mL). The extract was washed with brine and dried (Na$_2$SO$_4$). Filtration and concentration to dryness gave 1.6 g of the title compound.
$^1$H NMR (CDCl$_3$) δ 7.2–7.4 (m, 15H), 5.02 (br s, 1H), 3.6–3.7 (m, 1H), 3.18 (br s, 1H), 2.7–2.9 (m, 2H), 2.3–2.6 (m, 2H), 1.8–1.9 (m, 1H), 1.2–1.6 (m, 2H), 1.40 ( s, 9H), 0.8–0.95 (m, 6H).

Step D N-[2(R)-(t-butoxycarbonyl)amino-3-triphenyl methylmercaptopropyl]-L-isoleucine-phenethylamide The product of Step C (0.108 g, 0.2 mmol), 1-(3-dimethylaminopropyl)-3-ethylcarbodiimide (EDC) (0.042 g, 0.22 mmol), and 3,4-dihydro-3-hydroxy- 4-oxo-1,2,3-benzotriazine (HOOBT) (0.036g, 0.22 mmol) were dissolved in 4 mL of 1:1 EtOAc/CHCl$_3$ and stirred at ambient temperature for 0.5 hr. To this yellow solution was added phenethylamine (0.028 mL, 0.22 mmol) and diisopropylethylamine (0.038 mL, 0.22 mmol) and stirring was continued for 48 h. The solution was concentrated and the residue was partitioned between EtOAc and H$_2$O. The organic layer was washed with water, aqueous saturated NaHCO$_3$, brine, and dried (Na$_2$SO$_4$). Filtration and concentration followed by chromatography (SiO$_2$, EtOAc: hexane, 1:3) gave 0.09 g (69%) of the title compound.
$^1$H NMR (CDCl$_3$) δ 7.1–7.4 (m, 20H), 4.5–4.55 (m, 1H), 3.56–3.68 (m, 1H), 3.43–3.55 (m, 2H), 2.7–2.9 (m, 3H), 2.4–2.5 (m, 1H), 2.2–2.4 (m, 3H), 1.6–1.75 (m, 1H), 1.44 (s, 9H), 1.0–1.1 (m, 6H).

Step E  N-[2(R)-Amino-3-mercaptopropyl]-L-isoleucine-phenethylamide

The product of Step D (0.09 g, 0.14 mmol) was dissolved in 4 mL of 25% trifluoroacetic acid (TFA) in $CH_2Cl_2$ at ambient temperature, triethylsilane (0.089 mL, 0.56 mmol) was added and the solution was stirred for 3 h. The reaction mixture was concentrated and partitioned between EtOAc and aqueous saturated $NaHCO_3$ solution. The organic layer was washed with brine and dried ($Na_2SO_4$). Filtration, concentration and trituration with hexane provided 0.02 g (44%) of the title compound, mp 69°–73° C.

$^1$H NMR ($CDCl_3$) δ 7.2–7.4 (m, 5H), 7.07 (t, 1H, J=4 Hz), 3.5–3.6 (m, 2H), 3.0–3.1 (m, 1H), 2.75–2.9 (m, 4H), 2.4–2.65 (m, 3H), 1.7–1.8 (m, 1H), 1.4–1.5 (m, 1H), 1.0–1.2 (m, 1H), 0.8–0.95 (m, 6H). Mass spectrum (FAB) 324 (M+1). Anal. Calcd for $C_{17}H_{29}N_3OS$: C, 63.12; H, 9.04, N, 12.99. Found: C, 62.86; H, 9.42; N, 12.71.

Using the methods described in Example 1, the following compounds were prepared:

N-[2(R)-Amino-3-mercaptopropyl]-L-isoleucine-benzylamide_ bistrifluoroacetate salt, mp 70°–75° C.

$^1$H NMR (DMSO) δ 8.7–8.95 (m, 1H), 7.2–7.4 (m, 5H), 4.27–4.45 (m, 2H), 3.25–3.5 (m, 2H), 2.65–3.1 (m, 4H), 1.68–1.82 (m, 1H), 1.5–1.68 (m, 1H), 1.05–1.22 (m, 1H), 0.8–0.95 (m, 6H). Anal. Calcd for $C_{16}H_{27}N_3OS$ 2 $CF_3CO_2H$ . 0.75 $H_2O$: C, 43.59; H, 5.58; N, 7.63. Found: C, 43.40; H, 5.45; N, 7.62.

N-[2(R)-Amino-3-mercaptopropyl]-L-isoleucine-3-methylbutylamide bistrifluoroacetate salt, mp 53°–56° C.

$^1$H NMR ($CD_3OD$) δ 3.42–3.75 (m, 1H), 2.8–3.4 (m, 6H), 1.55–1.8,5 (m, 3H), 1.44 (q, 2H, J=6 Hz), 1.15–1.32 (m, 1H), 0.83–1.08 (m, 12H). Anal. Calcd for $C_{14}H_{31}N_3OS$.2 $CF_3CO_2H$ . 0.5 $H_2O$: C, 41.06; H, 6.51; N, 7.98. Found: C, 41.14; H, 6.27; N, 8.25.

N-[2(R)-Amino-3-mercaptopropyl]-L-isoleucine-3-phenylpropylamide bistrifluoroacetate salt, mp 62°–65° C.

$^1$H NMR ($CD_3OD$) δ 7.15–7.35 (m, 5H), 4.8–5.14 (m, 2H), 3.48–3.6 (m, 1H), 2.95–3.42 (m, 5H), 2.9 (t,2H, J=6 Hz), 2.65–2.75 (m, 2H), 1.65–1.95 (m, 4H) 1.2–1.38 (m, 1H), 0.9–1.08 (m, 6H). Anal. Calcd for $C_{18}H_{31}N_3OS$ . 2 $CF_3CO_2H$ . 0.5 $H_2O$: C, 45.98; H, 5.96; N, 7.31. Found: C, 45.90; H, 5.90; N, 7.48.

N-[2(R)-Amino-3-mercaptopropyl]-L-isoleucyl-L-phenylalaninol bistrifluoroacetate salt, mp 55°–60 ° C.

$^1$N NMR ($CD_3OD$) δ 7.15–7.32 (m, 5H), 4.2–4.35 (m, 1H), 3.56 (d, 2H, J=6 Hz), 3.23–3.35 (m, 1H), 3.14 (d, 1H, J=6 Hz), 2.95–3.04 (dd, 1H , J=12,6 Hz), 2.6–2.8 (m, 4H), 2.49–2.6 (d, 1H, J=6,15 Hz), 1.55–1.78 (m, 2H), 1.1–1.25 (m, 1H), .8–1.04 (m, 6H). Anal. Calcd for $C_{18}H_{31}N_3O_2S$ . 2 $CF_3CO_2H$ . 1.7 $H_2O$: C, 43.16; H, 5.99; N, 6.86. Found: C, 42.95; H, 5.60; N, 7.16.

N-[2(R)-Amino-3-mercaptopropyl]-L-isoleucine-N'-methylbenzylamide bistrifluoroacetate salt, mp 68°–73° C. Anal. Calcd for $C_{17}H_{29}N_3OS$ . 2.25 $CF_3CO_2H$: C, 44.52; H, 5.43; N, 7.24. Found: C, 44.48; H, 5.19; N, 7.26.

$^1$H NMR ($CD_3OD$) δ 7.18–7.45 (m, 5H), 4.68 (q, 2H), 3.5–3.78 (m, 2H), 2.9–3.2 (m, 6H), 2.69–2.70 (m, 1H), 1.6–1.8 (m, 2H), 1.1–1.28 (m, 1H), 0.85–1.18 (m, 6H).

N-[2(R)-Amino-3-mercaptopropyl]-L-isoleucine-(4-methoxybenzyl)amide bisftrifluoroacetate salt.

$^1$H NMR ($CD_3OD$) δ 7.24 (d, 2H, J=9 Hz), 6.88 (d, 2H, J=9 Hz), 4.35 (q, 2H), 3.77 (s, 3H), 3.32–3.4 (m, 1H), 3.15 (d, 1H, J=6 Hz), 2.99 (dd, 1H, J=4.5, 13.5 Hz), 2.74–2.86 (m, 3H), 1.6–1.76 (m, 2H), 1.14–1.24 (m, 1H), 0.88–0.94 (m, 6H). Mass spectrum (FAB) 340 (M+1). Anal. Calcd for $C_{17}H_{29}N_3O_2S$ . 2.1 $CF_3CO_2H$: C, 43.98; H, 5.41; N, 7.26. Found: C, 43.80; H, 5.35; N, 7.44.

N-[2(R)-Amino-3-mercaptopropyl]-L-isoleucine-(2,4-dichlorobenzyl)amide bistrifluoroacetate salt. $^1$H NMR ($CD_3OD$) δ 7.49 (d, 1H , J=3 Hz), 7.42 (d, 1H, J= 9 Hz), 7.32 (dd, 1H, J=3, 9 Hz), 4.49 (q, 2H), 3.32–3.38 (m, 1H), 3.14 (d, 1H, J=6 Hz), 2.98 (dd, 1H, J=4.5, 13.5 Hz), 2.85 (dd, 1H, J=6, 15 Hz), 2.78 (dd, 1H, J=6, 15 Hz). 2.76–2.8 (m, 1H), 1.6–1.74 (m, 2H), 1.14–1.24 (m, 1H), 0.89–0.95 (m, 6H). Mass spectrum (FAB) 378 (M+1). Anal. Calcd for $C_{16}H_{25}Cl_2N_3OS$ . 2.2 $CF_3CO_2H$: C, 38.94; H, 4.36; N, 6.68. Found: C, 38.63; H, 3.98; N, 6.81.

N-[2(R)-Amino-3-mercaptopropyl]-L-isoleucine-(4-trifluoromethylbenzyl)amide bistrifluoroacetate salt.

$^1$H NMR ($CD_3OD$) δ 7.64 (d, 2H, J - 7.5 Hz), 7.51 (d, 2H, J=7.5 Hz), 4.5 (q, 2H), 3.32–3.37 (m, 1H), 3.13 (d, 1H, J=6 Hz), 2.98 (dd, 1H, J=5, 13.5 Hz), 2.85 (dd, 1H, J=6, 15 Hz), 2.77 (dd, 1H, J=6, 15 Hz), 2 .75–2.8 (m, 1H), 1.61–1.76 (m, 2H), 1.16–1.26 (m, 1H ), 0.90–0.96 (m, 6H). Mass spectrum (FAB) 378 (M+1). Anal. Calcd for $C_{17}H_{26}F_3N_3OS$ . 2 $CF_3CO_2H$:C, 41.65; H, 4.66; N, 6.94. Found: C, 42.27; H, 4.53; N, 7.12.

N-[2(R)-Amino-3-mercaptopropyl]-L-isoleucine-( 2,4-dichlorophenethyl)amide bistrifluoroacetate salt.

$^1$H NMR ($CD_3OD$) δ 7.48 (d, 1H, J=2 Hz), 7.3–7.4 (m, 2H), 3.5–3.63 (m, 2H), 2.7–3.1 (m, 8H), 1.55–1.75 (m, 2H), 1.1–1.25 (m, 1H), 0.9–1.0 (m, 6H). Mass spectrum. (FAB) 392 (M+1). Anal. Calcd for $C_{17}H_{27}Cl_2N_3OS$ . 2 $CF_3CO_2H$: C, 40.65; H, 4.71; N, 6.77. Found: C, 40.90; H, 4.74; N, 6.89.

N-[2(R)-Amino-3-mercaptopropyl]-L-isoleucine-(2-benzimidazolylmethyl)amide bistrifluoroacetate salt.

$^1$H NMR ($CD_3OD$) δ 7.75–7.8 (m, 2H), 7.5–7.6 (m, 2H), 4.85 (q, 2H), 3.25–3.4 (m, 1H), 3.19 (d, 1H, J=6 Hz), 2.97 (dd, 1H, J=4.5, 9 Hz), 2.7–2.9 (m, 3H), 1.65–1.8 (m, 1H), 1.5–1.6 (m, 1H), 1.1–1.3 (m, 1H), 0.85–1.0 (m, 6H). Mass spectrum (FAB) 350 (M+1). Anal. for $C_{17}H_{27}N_5OS$ . 3 $CF_3CO_2H$ . $H_2O$: C, 38.93; H, 4.55; N, 9.87. Found: C, 38.74; H, 4.33; N, 9.89.

N-[2(R)-Amino-3-mercaptopropyl]-L-isoleucine-(1-indanyl)amide, mp 68°–71° C.

$^1$H NMR ($CD_3OD$) δ 7.15–7.35 (m, 4H), 5.4–5.5 (m, 1H), 2.7–3.1 (m, 8H), 2.45–2.6 (m, 1H), 1.85–2.0 (m, 1H), 1.55–1.7 (m, 2H), 1.0–1.3 (m, 2H), 0.9–1.05 (m, 6H). Mass spectrum (FAB) 336 (M+1). Anal. Calcd for $C_{18}H_{29}N_3OS$ . 2 $CF_3CO_2H$: C, 46.89; H, 5.54; N, 7.46. Found: C, 46.64; H, 5.39; N, 7.69.

N-[2(R)-Amino-3-mercaptopropyl]-L-isoleucine-(2,4-dimethylbenzyl)amide, mp 68°–73° C.

$^1$H NMR ($CD_3OD$) δ 7.15 (d, 1H, J=7 Hz ), 6.95–7.1 (m, 2H), 4.4 (q, 2H), 3.4–3.5 (m, 1H), 3.1 (dd, 1H, J=5, 12 Hz), 2.75–3.0 (m, 3H), 2.35 (s, 3H), 2.25 (s, 3H), 1.55–1.85 (m, 2H), 1.1–1.3 (m, 1H), 0.85–1.0 (m, 6H). Mass spectrum (FAB) 338 (M+1). Anal. Calcd for $C_{18}H_{31}N_3OS$ . 2 $CF_3CO_2H$ . $H_2O$: C, 45.27; H, 6.05; N, 7.20; Found: C, 45.23; H, 5.74; N, 7.21.

N-[2(R) -Amino-3-mercaptopropyl]-L-isoleucine-( 2,3-dichlorobenzyl)amide, mp 70°–74° C.

$^1$H NMR ($CD_3OD$) δ 7.5 (dd, 1H, J=1, 7 Hz), 7.4 (dd, 1H, J=1, 7 Hz), 7.3 (t, 1H, J=7 Hz), 4.55 (s, 2H), 3.35–3.5 (m, 1H), 3.05 (dd, 1H, J=6, 13 Hz), 2.75–2.95 (m, 3H), 1.55–1.85 (m, 2H), 1.1–1.3 (m, 1H), 0.85–1.05 (m, 6H). Mass spectrum (FAB) 378 (M+1). Anal. Calcd for $C_{16}H_{25}N_3OCl_2S$ . 2 $CF_3CO_2H$ . 0.5 $H_2O$: C, 39.03; H, 4.59; N, 6.83. Found: C, 39.08; H, 4.49; N, 6.76.

N-[2(R)-Amino-3-mercaptopropyl]-L-isoleucine-(4-sulfamoylbenzyl)amide, mp 65°–70° C.
$^1$H NMR (CD$_3$OD) δ 7.85 (d, 2H, J=8 Hz), 7.5 (d, 2H, J=8 Hz), 4.5 (q, 2H), 3.4–3.5 (m, 1H), 3.1 (dd, 1H, J=6, 13 Hz ), 2.75–3.0 (m, 3H), 1.55–1.9 (m, 2H), 1.15–1.3 (m, 1H), 0.85–1.05 (m, 6H). Mass spectrum (FAB) 389 (M+1). Anal. Calcd for C$_{16}$H$_{28}$N$_4$O$_3$S$_2$ . 2.5 CF$_3$CO$_2$H . 1.5 H$_2$O: C, 36.00; H, 4.82; N, 8.00. Found: C, 35.96; H, 4.51; N, 8.18.

Example 2

N-[2(R)-Amino-3-mercaptopropyl]-L-isoleucine-anilide
Step A N-[2(R)-(t-butoxycarbonyl)amino-3-triphenyl methylmercaptopropyl]-L-isoleucine-anilide To a solution of aniline (0.015 g, 0.16 mmol) and diisopropylethylamine (0.42 g, 0.32 mmol) in CH$_2$Cl$_2$ (3 mL) were added N-[2(R)-(t-butoxycarbonylamino)- 3-triphenylmethylmercaptopropyl]-L-isoleucine (0.84 g, 0.15 mmol) and bis(2-oxo-3-oxazolidinyl)-phosphinic chloride (BOP-Cl) (0.42 g, 0.165 mmol) with stirring under argon at ambient temperature. After stirring for 20 h the solution was diluted with EtOAc, washed with aqueous citric acid solution, aqueous saturated NaHCO$_3$ solution and brine. The solution was dried (Na$_2$SO$_4$) filtered and concentrated and the residue was purified by chromatography (SiO$_2$) (15% EtOAc/hexane) to provide 0.72 g (76%) of the title compound as a pale yellow gum. Mass spectrum (FAB) 638 (M+1).
Step B N-[2(R)-Amino-3-mercaptopropyl]-L-isoleucineanilide The product of Step A (0.07 g, 0.11 mmol) was deprotected using the method of Example 1, Step E to give 0.04 g (61%) of the title compound.
$^1$H NMR (CD$_3$OD) δ 7.56–7.6 (m, 2H), 7.3–7.6 (m, 2H), 7.1–7.16 (m, 1H), 3.4–3.48 (m, 1H), 3.08 (dd, 1H, J=5, 14 Hz), 2.79–2.92 (m, 3H), 1.72–1.86 (m, 2H), 1.24–1.31 (m, 1H), 1.03 (d, 3H, J=7 Hz), 0.96 (t, 3H, J=7 Hz). Mass Spectrum (FAB) 296 (M+1). Anal. Calcd for C$_{15}$H$_{25}$N$_3$OS . 2.6 CF$_3$CO$_2$H: C, 40.99; H, 4.70; N, 7.10. Found: C, 40.65; H, 4.51; N, 7.07.
Using the methods described in Example 2, the following compounds were prepared:
N-[2(R)-Amino-3-mercaptopropyl]-L-isoleucine-(2,4-dimethylphenyl)amide, mp 74°–76° C., sin 63° C.
$^1$H NMR (CD$_3$OD) δ 7.0–7.2 (m, 3H), 3.35–3.45 (m, 1H), 3.2–3.3 (m, 1H), 3.10 (dd, 1H, J=6, 12 Hz), 2.8–2.95 (m, 2H), 2.30 (s, 3H), 2.25 (s, 3H), 1.7–1.9 (m, 2H), 1.25–1.4 (m, 2H), 1.07 (d, 3H, J=7 Hz), 1.00 (t, 3H, J=7 Hz). Mass spectrum (FAB) 645 (M+1). Anal. Calcd for disulfide C$_{34}$H$_{56}$N$_6$O$_2$S$_2$ . 4 CF$_3$CO$_2$H . 2 H$_2$O: C, 44.36; H, 5.67; N, 7.39. Found: C, 44.32; H, 5.56; N, 7.34.
N-[2(R)-Amino-3-mercaptopropyl]-L-isoleucine-(2,3-dimethylphenyl)amide, mp 89°–93° C.
$^1$H NMR (CD$_3$OD) δ 7.05–7.15 (m, 3H), 3.15–3.4 (m, 2H), 3.1 (dd, 1H, J=5, 13 Hz), 2.75–2.95 (m, 3H), 2.3 (s, 3H), 2.15 (s, 3H), 1.7–1.9 (m, 2H), 1.25–1.4 (m, 1H), 1.1 (d, 3H, J=7 Hz), 0.95 (t, 3H, J=7 Hz). Mass spectrum (FAB) 324 (M+1). Anal. Calcd for C$_{17}$H$_{29}$N$_3$OS . 2.5 CF$_3$CO$_2$H . H$_2$O: C, 42.17; H, 5.39; N, 6.71. Found: C, 42.22; H, 5.18; N, 6.68.

Example 3

L-Cysteinyl-L-isoleucine-phenethylamide
Step A N-t-Butoxycarbonyl-L-isoleucine-phenethylamide To a solution of t-butoxycarbonyl-L-isoleucine (2.31 g, 0.01 mol) in DMF (20 mL) was added EDC (2.11 g, 0.011 mol), HOBT (1.49 g, 0.011 mol) and phenethylamine (1.38 mL, 0.011 mol) with stirring at ambient temperature. Triethylamine (1.53 mL, 0.011 mol) was added to adjust the pH of the mixture to 6.5. After 4 h the DMF was removed under reduced pressure and the residue was partitioned between EtOAc (50 mL) and water (50 mL ). The aqueous layer was extracted with EtOAc (2×50 mL). The combined organic phase was washed with 10% citric acid solution, aqueous saturated NaHCO$_3$ solution and brine. The solution was dried (Na$_2$SO$_4$), filtered and concentrated to give 3.12 g (93.%) of the title compound.
$^1$H NMR (CDCl$_3$) δ 7.2–7.4 (m, 5H), 6.02 (br s, 1H), 5.03 (br s, 1H), 3.87 (dd, 1H, J=6, 9 Hz), 3.45–3.7 (m, 2H), 2.84 (t, 2H, J=7 Hz), 1.8–1.9 (m, 1H), 1.45 (s, 9H), 0.9–1.1 (m, 2H), 0.87–0.9 (m, 6H).
Step B L-Isoleucine-phenethylamide hydrochloride Hydrogen chloride gas was bubbled into a solution of N-t-butoxycarbonyl-L-isoleucine-phenethylamide (3.1 g, 9.3 mmol) in EtOAc (200 mL) at −20° C. in a dry ice-acetone bath until TLC (EtOAc: hexane, 1:3) indicated complete loss of starting material. The solution was concentrated to dryness to give 2.5 g (100%) of the title compound, which was used without further purification.
Step C N-(t-Butoxycarbonyl)-S-triphenylmethyl)-L-cysteinyl-L-isoleucine-phenethylamide N-(t-Butoxycarbonyl)-S-triphenylmethyl)-L-cysteine (0.26 g, 0.55 mmol) was dissolved in DMF (3 mL) with EDC (0.11 g, 0.55 mmol), HOBT (0.074 g, 0.55 mmol) and L-isoleucine-phenethylamide hydrochloride (0.135 g, 0.5 mmol) at ambient temperature. The pH of the solution was adjusted to 6.5 with triethylamine (0.15 mL, 1.05 mmol ). After stirring for 16 h the solvent was evaporate d and the residue was partitioned between EtOAc (20 mL) and H$_2$O (20 mL). The aqueous layer was extracted with EtOAc (2×20 mL). The combined organic extract was washed with 10% citric acid solution, aqueous saturated NaHCO$_3$ solution, brine, and dried (Na$_2$SO$_4$). Filtration and concentration gave 0.285 g (87%) of the title compound after chromatography (SiO$_2$, EtOAc: hexane, 1:2).
$^1$H NMR (CDCl$_3$) δ 7.1–7.5 (m, 20H), 6.3–6.4 ( m, 2H ), 4.7–4.76 (m, 1H), 4.1–4.25 (m, 1H), 3.65–3.75 (m, 1H), 3.35–3.5 (m, 2H), 2.6–2.85 (m, 5H), 1.42 (s, 9H), 0.9–1.0 (m, 1H), 0.84–0.9 (m, 6H).
Step D L-Cysteinyl-L-isoleucine-phenethylamide The product of Step C (0.285 g, 0.43 mmol) was deprotected using the method of Example 1, Step E to give 0.145 g (75%) of the title compound as the trifluoroacetate salt, mp 156°–159° C.
$^1$H NMR (CD$_3$OD) δ 8.17–8.26 (m, 1H), 7.15–7.35 (m, 5H), 4.19 (d, 1H, J=7 Hz), 4.08 (t, 1H, J=6 Hz), 3.35–3.55 (m, 2H), 3.00 (d, 2H, 6 Hz), 2.82 (t, 2H, J=7 Hz ), 1.7–1.85 (m, 1H), 1.4–1.6 (m, 1H), 1.1–1.25 (m, 1H), 0.9–0.95 (m, 6H). Anal. Calcd for C$_{17}$H$_{27}$N$_3$O$_2$S . CF$_3$CO$_2$H: C, 50.54; H, 6.25; N, 9.31. Found: C, 50.75; H, 6.12; N, 8.81.

Example 4

N-[2(S)-[2(R)-Amino-3-mercaptopropylamino]-3 -methylpentyl]phenethylamine
Step A N-[2(S)-(2(R)-t-Butoxycarbonylamino-3-triphenylmethylmercaptopropylamino)-3 -methylpentyl]phenethylamine N-(t-Butoxycarbonyl)-S-triphenylmethyl)-L-cysteinyl-L-isoleucine-phenethylamide (0.33 g, 0.5 mmol) in THF (10 mL) was added dropwise to a suspension of lithium aluminum hydride (0.044 g, 1.2 mmol) in THF (10 mL) at ambient temperature under argon, and the mixture was heated at reflux for 18 h. After cooling, the reaction was quenched with 10% sodium potassium tartrate solution (10 mL) and stirred for 4 h. The mixture was filtered, concentrated, and partitioned between EtOAc and H$_2$O. The organic layer was separated, washed with aqueous saturated NaHCO$_3$ solution and brine. The solution was dried (Na$_2$SO$_4$), filtered and concentrated gave 0.1 g (31%) of the title compound after chromatography (SiO$_2$, CH$_2$Cl$_2$/MeOH, 9:1)
$^1$H NMR (CD$_3$OD) δ 7.2–7.45 (m, 20 H), 3.5–3.6 (m, 1H), 3.15–3.3 (m, 2H), 3.0–3.1 (m, 2H), 2.5–2.7 (m, 3H), 2.3–2.4 (m, 2H), 2.15–2.25 (m, 1H), 1.6–1.7 (m, 1H), 1.48 (s, 9H), 1.2–1.4 (m, 2H), 0.9–1.0 (m, 1H), 0.97 (t, 3H, J=7 Hz), 0.83 (d, 3H, J=7 Hz). Mass spectrum (FAB) 652 (M+1).
Step B N-[2(S)-[2(R)-Amino-3-mercaptopropylamino]-3-methylpentyl]phenethylamine The product of Step A (0.1 g, 0.16 mmol) was deprotected using the method of Example 1, Step E. The product was purified by partitioning between hexane and H$_2$O containing 0.1% TFA. The aqueous layer was separated and lyophilized to give 0.062 g (66%) of the title compound as the disulfide.
$^1$H NMR (CD$_3$OD) δ 7.2–7.4 (m, 10 H), 3.6–3.7 (m, 2H), 2.9–3.3 (m, 8H), 2.75–2.9 (m, 6H), 1.75–1.9 (m, 2H), 1.2–1.5 (m, 4H), 1.00 (t, 6H, J=7 Hz), 0.89 (d, 6H, J=7 Hz). Mass spectrum (FAB) 617 (M+1). Anal. Calcd for C$_{34}$H$_{60}$N$_6$S$_2$ . 5 CF$_3$CO$_2$H:02H: C, 44.52; H, 5.52; N, 7.08. Found: C, 44.16; H, 5.64; N, 7.32.

Example 5

Preparation of N-(2(R)-amino-3-mercaptopropyl)-L-alanine-benzylamide trifluoroacetate salt
Step A N-t-Butoxycarbonyl-L-alanine benzylamide N-t-Butoxycarbonyl-L-alanine (377 mg, 2.0 mmol), HOBT (283 mg, 2.1 mmol) and EDC hydrochloride (420 mg, 2.2 mmol) were dissolved in 5 mL of DMF. Benzylamine (230 μL, 2.1 mmol) was added followed by triethylamine (280 μL, 1.9 mmol). The mixture was stirred overnight and the solvent was evaporated. The residue was partitioned between ethyl acetate and 10% citric acid and the organic phase was washed sequentially with 10% sodium bicarbonate and brine. The solution was dried and evaporated to yield 498 mg of a waxy solid.
$^1$H NMR (CDCl$_3$) δ 7.3 (m, 5 H), 6.54 (br s, 1H), 5.00 (br s, 1H), 4.44 (m, 2H), 4.18(m, 1H), 1.41 (s, 9H), 1.38 (d, 3H, J=7 Hz).
Step B Preparation of L-alanine-benzylamide hydrochloride The product of Step A was dissolved in ethyl acetate, cooled to −50° C. and the solution was saturated with HCl gas. The mixture was stirred until TLC analysis indicated the complete consumption of the starting material. The solvent was evaporated at room temperature to afford the solid hydrochloride.
Step C N-(3-triphenylmethylmercapto-2(R)-t-butoxycarbonylaminopropyl)-L-alanine-benzylamide The product of Step B (183 mg, 0.85 mmol) and 3-triphenylmethylmercapto-2-t-butoxycarbonylaminopropanal (229 mg, 0.57 mmol) were dissolved in 3 mL of methanol. Sodium cyanoborohydride (95%, 18.8 mg, 0.28 mmol) was added and the mixture was stirred overnight. The solvent was evaporated and the mixture was partitioned between water and ethyl acetate. The organic phase was washed with sodium bicarbonate and brine. The solution was dried and evaporated and the residue was chromatographed on silica gel (2% methanol in methylene chloride). A foamy solid was obtained weighing 106 mg.
$^1$H NMR (CDCl$_3$) δ 7.3 (m, 20 H), 4.8 (br s, 1H), 4.4 (m, 2H), 3.65 (br s, 1H), 2.8 (br s, 2H), 2.4 (m, 2H), 1.5 (m, 12H).
Step D N-(2(R)-amino-3-mercapto-propyl)-L-alanine-benzylamide trifluoroacetate salt The product of Step C (103 mg, 0.18 mmol) was dissolved in 6 mL of 25% TFA in methylene chloride and triethylsilane (73 L, 0.45 mmol) was added. After 1 hour the solvent was evaporated and the residue was triturated with hexane. The hexane insoluble product was purified by reverse phase HPLC (Waters C-18, 93:7:0.1 water/acetonitrile/TFA). The lyophilized product, mp 61°–68° C., weighed 43 mg.
1H NMR (CD$_3$OD) 7.3 (m,5 H), 4.42 (s, 2H), 3.78 (q, J=3.6 Hz, 1H), 3.55 (m, 1H), 3.22 (dd, J=13, 6 Hz, 1H), 3.12 (dd, J=13, 6 Hz, 1H), 2.90 (m, 2H), 1.48 (d, J=7 Hz, 3H). Anal. Calcd for C$_{13}$H$_{21}$N$_3$OS. 2 CF$_3$CO$_2$H. 0.57 H$_2$O: C, 40.38; H, 4.81; N, 8.31. Found: C, 40.34; H, 4.77; N, 8.43.

Using the methods described in Example 5, following compounds were prepared:
N-Benzyl-[2(S)-(2(R)-amino-3-mercapto-propyl)amino]-butyramide trifluoroacetate salt, mp 62°–66 ° C. Anal. Calcd for C$_{14}$H$_{23}$N$_3$OS. 2 CF$_3$CO$_2$H. 0.5 H$_2$O: C, 41.70; H, 5.05; N, 8.10. Found: C, 41.68; H, 5.03; N, 8.15.
N-(3-mercapto-2(R)-aminopropyl)-L-norleucine-benzyl amide trifluoroacetate salt, mp 60°–67° C. Anal. Calcd for C$_{16}$H$_{27}$N$_3$OS. 2 CF$_3$CO$_2$H. 0.84 H$_2$O: C, 43.47; H, 5.60; N, 7.60. Found: C, 43.46; H, 5.50; N, 7.54.
N-(3-mercapto-2(R)-aminopropyl)-L-norvaline-benzyl amide trifluoroacetate salt, mp 60°–67° C. Anal. Calcd for C$_{16}$H$_{27}$N$_3$OS. 2 CF$_3$CO$_2$H. 0.84 H$_2$O: C, 42.37; H, 5.37; N, 7.80. Found: C, 42.42; H, 5.21; N, 7.45.

Example 6

In vitro inhibition of ras farnesyl transferase

Farnesyl-protein transferase (Ftase) from bovine brain was chromatographed on DEAE-Sephacel (Pharmacia, 0–0.8 M NaCl gradient elution), N-octyl agarose (Sigma, 0–0.6 M Nacl gradient elution), and a mono Q HPLC column (pharmacia, 0–0.3 M NaCl gradient). Ras-CVLS at 3.5 μM, 0.25 μM [$^3$H]FPP, and the indicated compounds were incubated with this partially purified enzyme preparation. The Ftase data presented below is a measurement of the ability of the test compound to inhibit RAS farnesylation in vitro.

TABLE 2

Inhibition of RAS farnesylation by compounds of this invention*

| Compound | IC$_{50}$(nM) |
| --- | --- |
| N-[2(R)-Amino-3-mercaptopropyl]-L-isoleucine-3-chlorophenethyl-amide | 63 |
| N-[2(R)-Amino-3-mercaptopropyl]-L-isoleucine-2,3-dichlorobenzyl-amide | 25 |
| N-[2(R)-Amino-3-mercaptopropyl]-L-isoleucine-anilide | 63 |
| N-[2(R)-Amino-3-mercaptopropyl]-L-isoleucine-2,3-dimethylphenyl-amide | 35 |

*(IC$_{50}$ is the concentration of compound which gives 50% inhibition of FTase under the described assay conditions)

What is claimed is:

1. A compound which inhibits farnesyl-protein transferase of the formula:

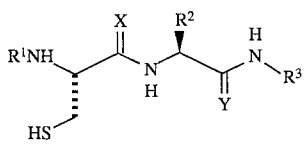

wherein:

X and Y are O;

R[1] is an alkyl group, hydrogen, an acyl group, an alkylsulfonyl group or arylsulfonyl group, wherein alkyl and acyl groups comprise straight chain or branched chain hydrocarbons of 1 to 6 carbon atoms which alternatively may be substituted with an aryl group;

R[2] is the side chains of naturally occurring amino acids, or in the alternative may be substituted or unsubstituted aliphatic, oraromatic groups, selected from the group consisting of allyl, cyclohexyl, phenyl, or saturated chains of 2 to 8 carbon atoms which may be branched or unbranched, wherein the aliphatic substituents may be substituted with an aromatic ring;

R[3] is an aromatic ring or in the alternative, an alkyl group or an aryl substituted alkane, wherein the aromatic ring is unsubstituted or in the alternative, substituted with one or more groups, selected from the group consisting of alkyl, halo, alkoxy, trifluoromethyl or sulfamoyl groups, and which may be polycyclic;

or the pharmaceutically acceptable salts thereof.

2. The compound according to claim 1 which inhibits farnesyl-protein transferase which is:

L-Cysteinyl-L-isoleucine-phenethyl amide.

3. A pharmaceutical composition comprising a pharmaceutical carrier, and dispersed therein, a therapeutically effective amount of a compound of claim 1.

4. A pharmaceutical composition comprising a pharmaceutical carrier, and dispersed therein, a therapeutically effective amount of compound of claim 2.

* * * * *